United States Patent [19]
Coombes et al.

[11] Patent Number: 6,001,395
[45] Date of Patent: Dec. 14, 1999

[54] POLYMERIC LAMELLAR SUBSTRATE PARTICLES FOR DRUG DELIVERY

[75] Inventors: Allan Gerald Arthur Coombes; Stanley Stewart Davis, both of Nottingham; Diane Lisa Major, London; John Michael Wood, Hertsfordshire, all of United Kingdom

[73] Assignee: Danbiosyst UK Limited, Nottingham, United Kingdom

[21] Appl. No.: 08/983,156

[22] PCT Filed: Jul. 15, 1996

[86] PCT No.: PCT/GB96/01695

§ 371 Date: Mar. 30, 1998

§ 102(e) Date: Mar. 30, 1998

[87] PCT Pub. No.: WO97/02810

PCT Pub. Date: Jan. 30, 1997

[30] Foreign Application Priority Data

Jul. 13, 1995 [GB] United Kingdom .................. 9514285

[51] Int. Cl.⁶ .............................. A61K 9/16; A61K 47/34
[52] U.S. Cl. .......................... 424/501; 424/426; 424/490
[58] Field of Search ..................................... 424/486, 426, 424/458, 428, 459, 490, 501; 514/952; 428/402, 402.24; 427/2.14

[56] References Cited

U.S. PATENT DOCUMENTS

| 4,492,720 | 1/1985 | Mosier . |
| 5,827,531 | 10/1998 | Morrison et al. . |
| 5,869,103 | 2/1999 | Yeh et al. . |

FOREIGN PATENT DOCUMENTS

| WO 95/11010 A1 | 4/1995 | WIPO . |
| WO 95/35097 A1 | 12/1995 | WIPO . |

OTHER PUBLICATIONS

Alpar, et al., "Identification of Some of the Physico–Chemical Characteristics of Microspheres which Influence the Induction of the Immune Response Following Mucosal Delivery," *Eur. J. Pharm. Biopharm.* 40(4):198–202 (1994).

Cohen, et al., "The pharmacokinetics of, and humoral responses to, antigen delivered by microencapsulated liposomes," *Proc. Natl. Acad. Sci. USA* 88:10440–44 (1991).

Eldridge, et al., "Biodegradable Microspheres as a Vaccine Delivery System," *Mol. Immunol.* 28(3):287–94 (1991).

Esparza, et al., "Parameters affecting the immunogenicity of microencapsulated tetanus toxoid," *Vaccine* 10(10):714–20 (1992).

Gray, et al., "B–cell memory is short lived in the absence of antigen," *Nature* 336:70–73 (1988).

Kalb, et al., "General crystalliazation behavior of poly(L–lactic acid)," *Polymer* 21(6):607–12; ACS Abstract No. 93:240075 (1980).

Khan, et al., "Immunopotentiation and Delivery Systems for Antigens for Single–Step Immunization: Recent Trends and Progress," *Pharm. Res.* 11(1):2–11 (1994).

Kreuter, et al., "Influence of hydrophobicity on the adjuvant effect of particulate polymeric adjuvants," *Vaccine* 6(3):253–56 (1988).

O'Hagan, et al., "Biodegradable microparticles as controlled release antigen delivery systems," *Immunology* 73(2):239–42 (1991); ACS Abstract No. 115:56995 (1991).

(List continued on next page.)

*Primary Examiner*—Edward J. Webman
*Attorney, Agent, or Firm*—Arnall Golden & Gregory, LLP

[57] ABSTRACT

The invention provides a composition for delivery of an active agent comprising a plurality of lamellar particles of a biodegradable polymer which is at least in part crystalline, and an active agent adsorbed to at least most of the particles. Preferably the biodegradablepolymer is at least 5% by weight crystalline. Preferred biodegradable polymers are poly(L-lactide) (L.PLA) or copolymers or blends of L.PLA. The particles are especially useful for the immobilization of antigens or allergens for vaccines.

18 Claims, 4 Drawing Sheets

OTHER PUBLICATIONS

O'Hagan, et al., "Long term antibody responses in mice following subcutaneous immunization with ovalbumin entrapped in biodegradable microparticles," *Vaccine* 11(9):965–69 (1993).

Park, et al., "Importance of in vitro experimental conditions as protein release kinetics, stability and polymer degradation in protein encapsulated poly(D,L–lactic acid–co–glycolic acid) microspheres," *J. Controlled Rel.* 33:211–22 (1995).

Raghuvanshi, et al., "Biodegradable delivery system for single step immunization with tetanus toxoid," *Int. J. Pharm.* 93:R1–R5 (1993).

Sharif, et al., "Biodegradable microparticles as a delivery system for the allergens of Dermatophogoides pteronyssinus (house dust mite): I. Preparation and characterization of microparticles," *Int. J. Pharm.* 119(2):239–46; ACS Abstract No. 122:298951 (1995).

Stieneker, et al., "Comparison of 24 different adjuvants for inactivated HIV–2 split whole virus as antigen in mice: Induction of titres of binding antibodies and toxicity of the formulations," *Vaccine* 13(1):45–53 (1995).

POLYMERIC LAMELLAR SUBSTRATE PARTICLES FOR DRUG DELIVERY

Priority is claimed under 35 U.S.C. § 119 to PCT/GB96/01695, filed Jul. 15, 1996, which corresponds to GB 9514285.7, filed Jul. 13, 1995.

The present invention relates to a composition for delivery of an active agent, and more particularly to a composition comprising lamellar polymeric particles.

BACKGROUND OF THE INVENTION

Systems for delivering pharmaceutically or therapeutically active agents, especially antigens, are of considerable interest.

Although the influence of factors such as the dose, formulation and frequency of administration of antigen on the immune response is recognised, optimal delivery and presentation have not in general been established (Khan et al 1994). In conventional liquid dosing regimens, several small doses of antigen are more effective than a single inoculation or a few large doses in stimulating a protective immune response. It is also known that protein concentrations as low as 0.001 μg are sufficient to stimulate a secondary response and that immunological unresponsiveness (tolerance) can be induced by both high and low doses of antigen and by frequent administration.

Many purified, synthetic or inactivated antigens such as Tetanus toxoid are poorly immunogenic and usually require several parenteral doses to confer adequate protection. Adsorption of vaccine antigens onto adjuvants such as Alum is a common method for enhancing the immunogenicity. A wide variety of substances, both biological and synthetic, have been used as adjuvants including mycobacteria, oil emulsions, liposomes, polymer microparticles and mineral gels. A range of 24 different adjuvants was recently investigated by Stieneker et al (1995) for inactivated HIV virus encompassing many of the adjuvant systems currently under investigation. However, only Aluminium hydroxide "Alum" has been approved for administration in humans but its use is often associated with adverse reactions.

As well as protecting antigens, stimulating phagocytosis and activating lymphoid cells, some adjuvants function by retaining the antigen at the site of deposition. Antigen retention appears vital for repeated stimulation of the memory B-cell population and for maintaining antibody titres over long periods (Gray et al 1988). The adjuvant effect of water-in oil emulsions Freund's Complete Adjuvant (FCA)/Freund's Incomplete Adjuvant (FIA), for example, is considered to arise from creation of a short-term 'depot effect' involving antigen retention as a result of granuloma formation. Malarial antigen has been detected at the injection site 80 days post-administration when formulated with liposomes and encapsulated in alginate poly(L-lysine) microparticles (Cohen et al 1991) suggesting that this system also provides a 'depot-type' vaccine for sustained retention and presentation of antigens to the immune system.

The considerable research effort devoted to vaccine formulation has generated a multitude of strategies for optimising antigen release rates and achieving single dose delivery systems. Pulse release of antigen from biodegradable, biocompatible poly(lactide co-glycolide) [PLG] microparticles is considered advantageous for stimulating the conventional, multi-dose, schedule. However, most microparticulate delivery systems are considered to function on the principle of sustained, long term antigen release which presents a continuous trickle of antigen to the immune system to maintain proliferation of immune cells and antibody production. Raghuvanshi et al (1993) developed a single injection formulation for Tetanus toxoid (TT) based on this principle using PLG microparticles. The resultant immune response over 5 months in rats was comparable with the conventional 2-dose schedule of TT adsorbed on alum.

The lower primary response observed with TT adsorbed to Alum was considered due to rapid antigen depletion resulting in reduced proliferation of immune cells.

The ability of small antigen-loaded PLG microparticles (<5 μm in size) to function as potent antigen delivery systems after sub-cutaneous administration is considered to arise from 2 mechanisms: 1) efficient phagocytosis resulting in transport to the lymph nodes where efficient antigen processing and presentation to T-helper cells occurs and 2) controlled release of antigen from the microparticles. (Eldridge et al 1991 O'Hagan et al 1991). However, high immune responses have also been induced using large (72 μm) protein-loaded microparticles (O'Hagan et al 1993) demonstrating that phagocytosis and transport to lymph nodes is not absolutely necessary for achieving high serum antibody titres. However, it is recognised that antigen-containing fragments from large microparticles could be phagocytosed.

It is acknowledged that the higher immune response obtained when using antigen-loaded PLG microparticles could be attributed to an adjuvant effect rather than to slow release of encapsulated protein since antigens adsorbed onto microparticles have been shown to generate potent immune responses after subcutaneous (O'Hagan et al 1993. Kreuter et al 1988) and nasal administration (Alpar and Almeida 1994).

SUMMARY OF THE INVENTION

It has now surprisingly been found that by using biodegradable polymers which are at least partially crystallisable, lamellar substrate particles can be produced which are at least in part crystalline, and which have been found to give improvements in adsorption of antigen, retention of antigen in vitro and improvement in immune response to adsorbed antigens.

The present invention therefore provides a composition for delivery of an active agent comprising a plurality of lamellar particles which particles comprise a biodegradable polymer which is at least in part crystalline, and an active agent adsorbed to at least most of the particles.

DETAILED DESCRIPTION OF THE INVENTION

Figure 1:
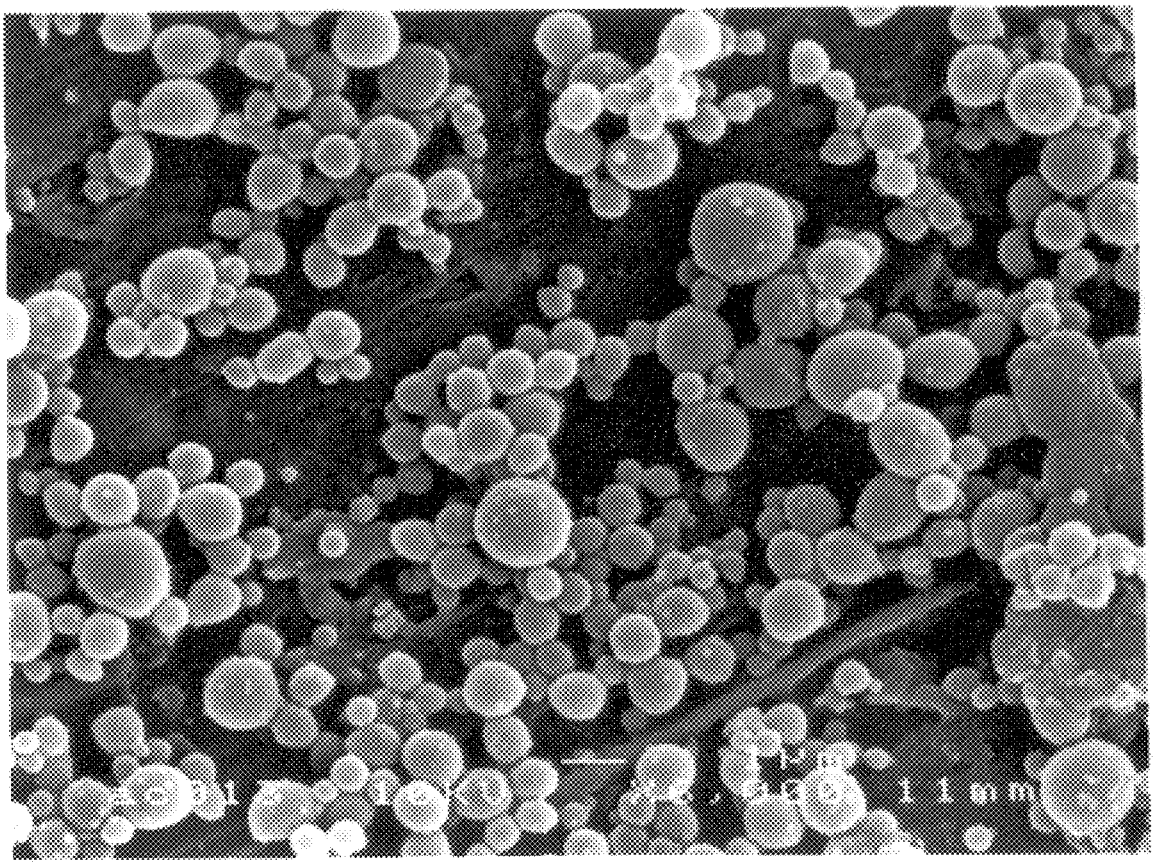
FIG. 1 is an electron micrograph of prior art spherical particles of poly(DL-lactide-co-glycolide) (PLG).
Figure 2:
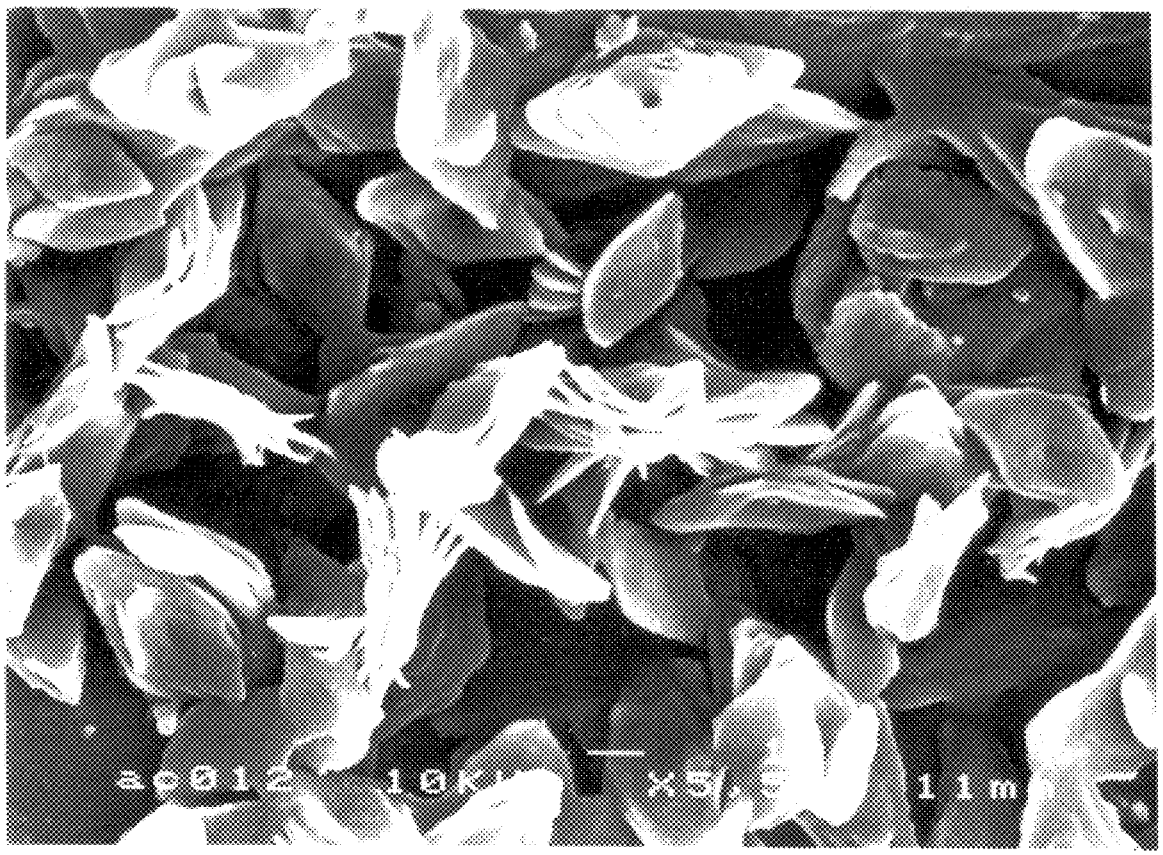
FIG. 2 is an electron micrograph of L-PLA lamellar particles in accordance with a preferred embodiment of the disclosed composition.
Figure 3:
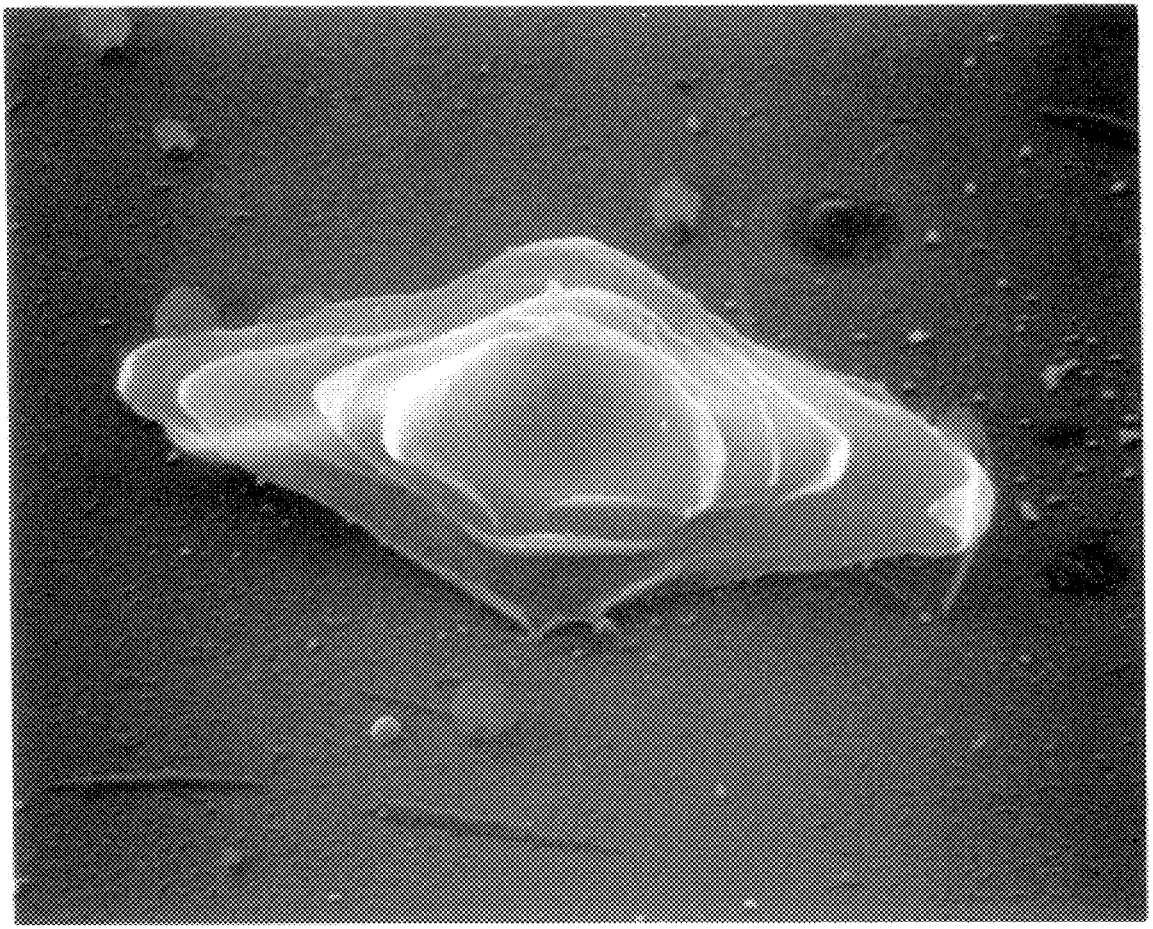
FIGS. 3 and 4 are electron micrographs of the lamellar systems without (FIG. 3) and with (FIG. 4) adsorbed influenza virus.
Figure 4:
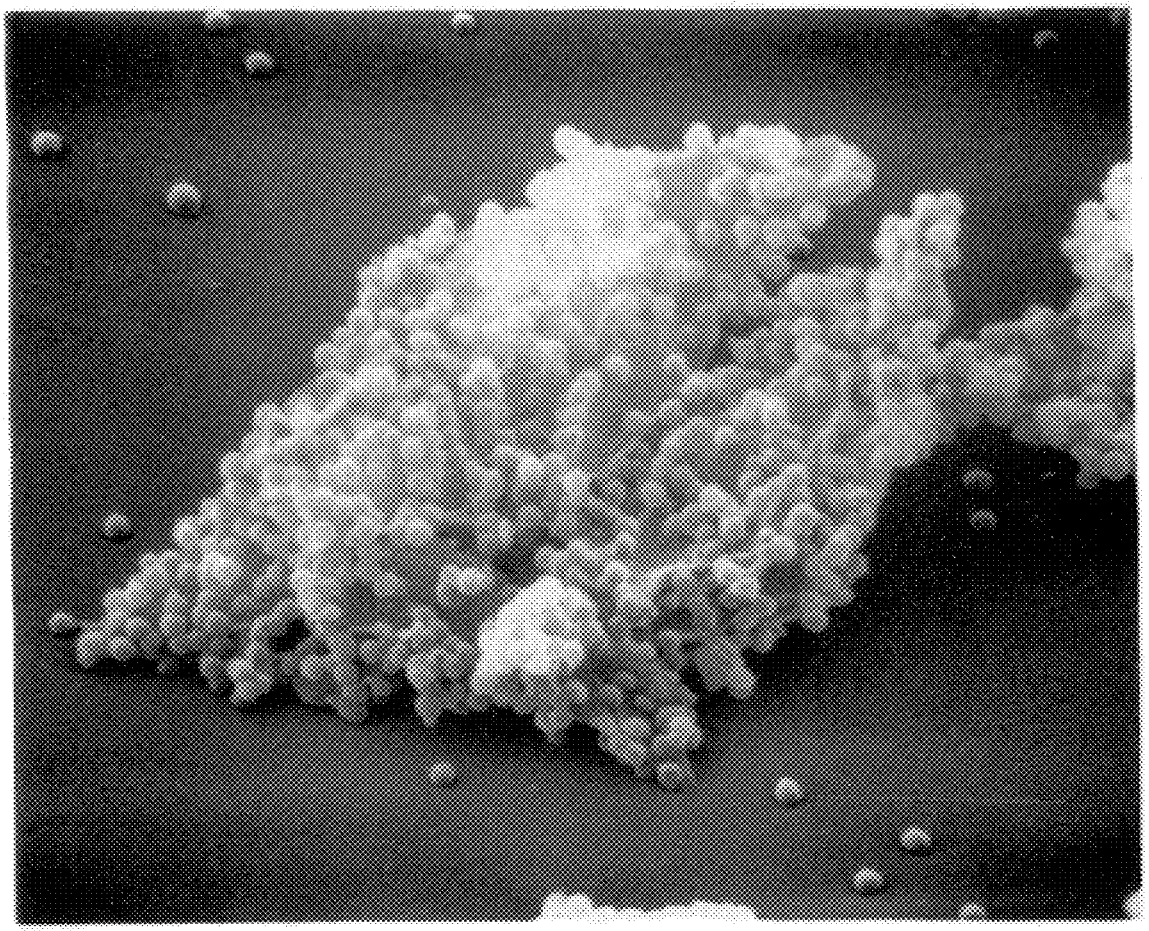

The term "biodegradable polymer" includes polymeric systems at least a part of which can degrade into low molecular weight compounds which are known to be involved normally in metabolic pathways. The term also includes polymer systems which can be attacked in the biological milieu so that the integrity of the system, and in some cases of the macromolecules themselves is affected and gives fragments or other degradation by-products which can move away from their site of action, but not necessarily from the body.

The biodegradable polymer used is preferably at least 5 percent by weight crystallisable.

The biodegradable polymer in the particle is preferably at least 5 percent by weight crystalline, more preferably at least 30%, more preferably at least 50%, at least 70% and most preferably at least 90% crystalline.

Whether or not a polymer is crystalline, and the degree of crystallinity, can be determined by methods well known in the art, for example X-ray diffraction methods as applied to polymers or by differential scanning calorimetry.

A preferred polymer is poly(L-lactide) (L.PLA) which is semi-crystalline in nature. The molecular weight of the L.PLA polymer is preferably in the range 2,000 to 100,000.

The polymer may a mixture of L.PLA with another biodegradable polymer or with a biocompatible but non-degradable polymer, either as a copolymer or as a blend of polymers. In either case, the resulting mixture should still be at least in part crystalline and preferably at least 5% by weight crystalline. The content of a non-crystallisable or non-crystalline polymer component should therefore be limited as necessary.

Suitable copolymers are copolymers of L.PLA and other poly($\alpha$-hydroxy acids) such as DL lactide or glycolide (eg. PLG), crystallisable copolymers of lactic acid and lactone, copolymers of L-lactide and poly(ethylene glycol) [PEG], copolymers of L-lactide and $\alpha$-amino acids (polydepsipeptides), polyanhydrides, and polyorthoesters.

Suitable blends of L.PLA with other polymers include other poly($\alpha$-hydroxy acids) such as poly(DL lactide co-glycolide), PEG, copolymers of polyethylene oxide and polypropylene oxide (PEO-PPO), polydepsipeptides, polyorthoesters, polyanhydrides, polyphosphazene and copolymers of acrylic and methacrylic acid esters (EUDRAGIT™).

Other biodegradable synthetic polymers potentially useful for preparing lamellar substrates include copolymers of $\alpha$-hydroxy acids, $\alpha$-amino acids (polydepsipeptides), polyhydroxybutyric acid, copolymers of lactic acid and lactone, copolymers of lactic acid and PEG, copolymers of hydroxybutyrate and hydroxyvalerate, polyethylene terephthalate, polyphosphazenes, polycaprolactone, polyorthoesters, polyanhydrides and copolymers thereof or blends of such polymers.

By "lamellar" it is meant that the particles comprise thin plates or layers; lipsomes are not lamellar particles of the invention.

It is preferred if the lamellar particles are irregularly shaped as may be formed using some of the methods in the Examples.

The lamellar particles are often "lozenge-shaped", and may be present in the composition as discrete lamellar particles, or as sheave-like, polyhedral particles formed by lamellae which are coalesced together along a common plane. The term "lamellar particle" is used to include both possibilities. The lamella particle thickness is in the range 50 nm to 80 $\mu$m, but is preferably in the range 50 to 500 nm. The lower end of the range corresponds to single lamellar particles that have substantially flat surfaces and the upper end corresponds to stepped or coalesced lamellar particles. The surface of the lamella often exhibits a stepped topography which is typical of polymer crystal growth.

The plan dimensions of the lamellar particles, both width and length, are typically in the range 0.5 $\mu$m to 80 $\mu$m, preferably 1 $\mu$m to 40 $\mu$m, more preferably 1 $\mu$m to 10 $\mu$m and most preferably 3 $\mu$m to 5 $\mu$m. The aspect ratio, the ratio of length to width, is in the range 160:1 to 1:1, more preferably 2.5:1 to 3:2.

The particle morphology can be measured using scanning electron microscopy and atomic force microscopy.

The term "active agent" is used herein to include any agent which it may be desired to administer to the human or animal body for any purpose, including therapeutic, pharmaceutical, pharmacological, diagnostic, cosmetic and prophylactic agents and immunomodulators.

Active agents include growth hormone such as bone morphogenic protein (BMP), insulin, interferons (alpha, beta, gamma), erythropoietin, colony stimulating factor such as granulocyte macrophage colony stimulating factor (GM-CSF), interleukin 2 and 12, parathyroid hormone, leutenising hormone releasing hormone, calcitonin, heparin, somatropin and various analogues thereof. Nucleic acid, which includes oligonucleotides as small as 10 nucleotides in length, is also included in the term "active agent".

The active agent is preferably a vaccine, antigen or allergen or DNA.

Tetanus toxoid and influenza virus are especially preferred.

Antigens include polypeptides, proteins, glycoproteins and polysacchraides that are obtained from animal, plant, bacterial, viral and parasitic sources or produced by synthetic methods. The term antigen includes any material which will cause an antibody reaction of any sort when administered. Such antigens can be administered by injection or to various mucosal sites (nasal, oral, vaginal, rectal, colonic).

Vaccines for the treatment of allergens and for auto immune diseases are well described in the prior art. For example in autoimmune disease it has been suggested that the slow administration of essential factors can be beneficial. Such factors can include insulin for the treatment of diabetes and collagen for treating rheumatoid arthritis.

The active agent may also be a polypeptide, peptide or protein, a carbohydrate or an oligonucleotide such as DNA, including growth hormone, insulin, interferons (alpha, beta, gamma), interleukins erythropoietin, colony stimulating factors, growth factors, parathyroid hormone, leutenizing hormone releasing hormone, calcitonin, heparin, somatostatin and various analogues thereof.

The active agent is adsorbed onto or into the lamellar particles after preparation thereof by admixing the agent with the particles.

If the active agent is a peptide or protein drug, the lamellar particle, with the adsorbed active agent, is preferably encapsulated or enteric coated with polymer such as poly (D,L-lactide co-glycolide) (PLG) or a EUDRAGIT™ polymer, prior to oral administration.

Adjuvants immobilised on lamellae may be co-administered with immobilised antigens by mixing two populations of lamellae. Adjuvants include dextran sulphate, synthetic analogies of mycobacterial fragments (muramyl dipeptide, lauroyltetrapeptide), muramyl tripeptide phosphatidylethanolamine (MTP-PE), monophosphoryl lipid derived from bacterial endotoxin (MPL A), chitosan and its oligomers.

The lamellar surface may be modified to improve interaction of the substrate with bioactive agents.

The lamellar surface may be modified to improve interaction of the substrate with host cells and tissue.

The lamellar surface may be modified to improve interaction of the substrate with bioactive agents.

Modification of the surface characteristics of the lamellae may be desirable so as to attract particular molecules, ligands or to modulate the interaction of the lamellae with host cells and tissues.

In one instance, chances to the immonomodulatory character of the lamellae may be desirable to stimulate a particular type of response. TH1 lymphocytes are predominantly associated with cell mediated immunity (essential for recognition and killing of virus or bacteria infected cells) producing cytokines such as IL-2 and IFN-γ. TH2 cells are associated with antibody production and humoral immune responses producing cytokines such as IL-4 and IL-10. Co-administration of cytokine-modified lamellae and antigens may be useful for conferring protection against infectious agents of viral and bacterial origin.

The lamellae may be modified by a molecule recognised by, and having an affinity for, a particular cellular receptor in the human or animal body to provide a targeting potential. The attachment of lectins or monoclonal antibodies to the surface of lamellae could be useful for improving interaction with the mucosal surface of the gastrointestinal tract.

Polymeric surface modifiers may be attached to the lamellae by adsorption, by physical chain entanglement and interpenetration with the surface or by chemical grafting.

The surface modifier may be added to the non-solvent used for precipitation of the lamellae in process stage (b) (see below). Alternatively, the solid substrate may be treated after production.

Surface modifying polymers include the block copolymers based on polyethylene oxide and polypropylene oxide (POLOXAMERS™, POLOXAMINES™) and tetrafunctional block copolymers derived from the sequential addition of propylene oxide and ethylene oxide to ethylene diamine (POLOXAMINES™), polyvinylalcohol, polyvinylpyrrolidone, sorbitan esters such as sorbitan monostearate (SPAN 60™), polysorbates (TWEEN™), polyoxyethylene fatty esters, phospholipids such as lecithin, lysophosphatidylcholine (LPC), fatty acids, stearic acid, stearates and their derivatives with for example, polyoxyethylene.

Other polymers potentially useful for surface modification include the polyamidoamines, polymalic acid, polyamino acids, poly(L-lysine), poly(L-glutamic acid), poly(L-aspartic acid) and their copolymers, polymers of acrylic acid (CARBOPOL™) and copolymers based on maleic anhydride.

Other categories of surface modifying agents include the anionic detergents, sodium salts of deoxycholic acid, glycocholic acid or sodium lauryl sulfate (SDS), cationic detergents and non-ionic detergents such as polyoxyethylene ether, which is sold under the trademark TRITON™ (Union Carbide Ltd.).

Surface modifying polymers may also be selected from the group comprising protein and polysaccharides whether natural or synthetically made and their derivatives such as conjugates with polyethylene glycol PEG.

The term protein is intended to include peptides, polypeptides glycoproteins, metalloproteins, lipoproteins and subunits or fragments thereof. Proteinaceous materials include albumin, gelatin, collagen, glycoproteins and their derivatives with, for example, polyethylene glycol. Methods for preparing conjugates of PEG and protein have been described by Nucci et al in Advances in Drug Delivery Reviews, 6 113–151 (1991).

The term polysaccharides includes polymers of amino sugars.

Examples of polysaccharides useful as surface modifiers include dextran, xanthan, chitosan, chitosan lactate, chitosan glutamate, pectin, dextrin, maltodextrin, hyaluronic acid, cellulose, starch, hydroxyethyl starch, pullulan, inulin, alginates, heparin and heparin-like synthetic polymers and their respective derivatives. Conjugates of PEG and polysaccharides for example have been described by Duval et al in Carbohydrate Polymers, 15 233–242 (1991).

The surface modifier may be a mixture of two or more of the types of polymer listed above.

The lamellae may be adapted for injection either intramuscularly, intravenously, subcutaneously, intraarticularly or intraperitoneally. They will generally be sterile and pyrogen-free. The lamellae may be adapted for administration to the dermal or epidermal layer of the skin by injection or needleless injector system. The lamellae may also be adapted for administration to mucosa such as the nose, the gastrointestinal tract, the colon, the vagina and the rectum.

The lamellar particles of the invention can be formulated in ways well known in the art.

The formulations may conveniently be presented in unit dosage form and may be prepared by any of the methods well known in the art of pharmacy. Such methods include the step of bringing into association the lamellar particles to which the active agent has been adsorbed with the carrier which constitutes one or more accessory ingredients. In general the formulations are prepared by uniformly and intimately bringing into association the said lamellar particles with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formation isotonic with the blood of the intended recipient; and aqueous and non-aqueous sterile suspensions which may include suspending agents and thickening agents. The formulations may be presented in unit-dose or multi-dose container, for example sealed ampoules and vials, and may be stored in a freeze-dried (lyophilised) condition requiring only the addition of the sterile liquid carrier, for example water for injections, immediately prior to use.

Extemporaneous injection solutions and suspensions may be prepared from sterile powders, granules and tablets of the kind previously described.

Preferred unit dosage formulations are those containing a daily dose or unit, daily sub-dose or an appropriate fraction thereof, of an active ingredient.

It should be understood that in addition to the ingredients particularly mentioned above the formulations of this invention may include other agents conventional in the art having regard to the type of formulation in question.

The amount of the lamellar particle composition of the invention to be administered to a patient may be determined in relation to the amount of active agent to be administered and to the amount of active agent adsorbed on the said particle and to the way in which the active agent becomes available in the patient following administration of the composition.

Suitably, the amount of the composition administered would be that which contains between 1% and 1000% of the normal amount of the active agent administered to the patient when administered in a conventional way. Preferably, the amount contains between 10% and 500% of the normal amount of the active agent; more preferably between 20% and 80%.

For nasal administration, the vaccines can be administered as a fine suspension using a spray device or if in the form of a powder using a powder device or nasal insufflator. Such devices are well familiar to those skilled in the art. Formulations for the gastrointestinal tract can be administered as suspensions or formulated as tablets and capsules or into compressed or extruded pellets.

For surface adsorbed antigens that are sensitive to the acid conditions in the stomach the delivery system can be protected by an enteric polymer familiar to those skilled in the art of formulation. The enteric polymer can be used to coat the dosage form. Vaginal systems suitable for delivery include gels and vaginal suppositories. Rectally administrated vaccines can be given as enemas or incorporated into suppositories.

A method for making the compositions described herein includes the following steps:

a) dissolving the polymer in a solvent;
b) stirring the polymer solution vigorously and adding a non-solvent for the polymer;
c) evaporating the solvent from the mixture of step (b); and
d) admixing an active agent with the thus formed particles.

It has been found that by using crystallisable polymers, the above precipitation method will form lamellar particles, in contrast to the prior art spherical particles formed using amorphous polymers.

The solvent used, which is a "poor solvent" for the biodegradable polymer, is preferably acetone, ethyl acetate, xylene or dioxane, although any other suitable solvent may be used. Heat may need to be applied to dissolve the polymer in the solvent. The non-solvent is preferably water, methanol or ethanol.

By "poor" solvent we mean a solvent in which the polymer has a low or negligible solubility so that the polymer will come out of solution as a (partly) crystalline material (precipitation process). The solvents and non-solvents for polymers can be found in standard texts (eg. see Fuchs, in Polymer Handbook, 3rd Edition) and Deasy, Microencapsulation and Related Drug Processes, 1984, Marcel Dekker, Inc., New York.

The ability of a polymer to dissolve in a solvent can be estimated using the Cohesive Energy Density Concept (CED) and related solubility parameter values as discussed by Deasy and to be found in detail in the article by Grulke in Polymer Handbook.

Thus a person skilled in the art will be able to select a "poor" solvent to give the required precipitation of the lamellar material.

The lamellar particles may also be made by a crystallization method in which the polymer is dissolved in the solvent as before, cooled and left to crystallize. The particles can then be harvested by filtration. The thus-formed particles are then admixed with the active agent to form a composition according to Claims 1 to 12.

It has been found that the lamellar particles of the invention provide a greatly increased adsorption of active agents compared with prior art spherical particles formed from amorphous polymers. The adsorption of active agents onto lamellar particles also avoids the disadvantages found with prior art microencapsulated vaccines based on PLG. These include avoidance of exposure to high shear forces and solvents and acid degradation products produced by PLG which may denature certain antigens. Furthermore, the lamellar particles have been found to have much greater retention of the antigen over long time periods in vitro. It is thought that the irregular lamellar form of the particles may function as an immunomodulator and stimulate the immune system.

When used in animal studies to measure the immune response to absorbed influenza virus, the lamellar particles of the invention resulted in 60% of challenged mice being protected.

Preferred embodiments of the composition are described in detail in the following examples.

EXAMPLE 1

Production of Lamellar Substrate Particles by Precipitation 10 ml of water was injected into 5 ml of a 2% (w/w) PLA solution in acetone which was stirred vigorously with a magnetic stirrer. The molecular weight of PLA was 6600.

The mixture was then gently stirred overnight with a magnetic stirrer to evaporate the acetone solvent.

The resulting lamellar PLA particles can be harvested from the suspension by filtration, or the suspension may be stored at 5° C.

EXAMPLE 2

Production of Lamellar Substrate by Polymer Crystallisation from Solution under Quiescent Conditions The method has also been used to prepare L.PLA substrates from a 0.5% (w/v) acetone solution of a 100,000 Mw polymer as follows:

a) the L.PLA polymer was dissolved in acetone by heating to approximately 50° C.

b) the solution was allowed to stand at room temperature for 1 hour whereupon crystallisation occurred on cooling.

The resulting lamellar particles may be harvested by filtration.

EXAMPLE 3

Antigen Adsorption

25–30 mg of particles (accurately weighed) produced by the method of Example 1 were incubated in an aqueous solution of an antigen overnight at room temperature with end-over end shaking (Voss mixer). The microparticles were centrifuged and washed once with distilled water. The supernatants were collected and analysed for antigen content using a BCA protein assay. A calibration curve was constructed from a series dilution of the respective antigen and the quantity of antigen adsorbed on the lamellar substrates was obtained by subtraction. The adsorbed amounts of the antigen, influenza virus, Tetanus toxoid and ovalbumin respectively are presented in Table 1.

EXAMPLE 4

In Vitro Antigen Release from PLA Lamellar Substrate Particles

25–30 mg PLA lamellar particles with adsorbed antigen prepared according to Example 3 were incubated in 2 ml PBS containing 0.02% Sodium azide at 37° C. The release medium was separated from the microparticles after 1 day and fresh medium was added to the sample tubes. This process was repeated at 3 day intervals up to 8 weeks. The release medium was analysed for antigen content using a BCA protein assay and the cumulative release amount of antigen (%) calculated. The retained amounts of Influenza virus, Tetanus toxoid and ovalbumin respectively are presented in Table 1.

TABLE 1

Adsorption of antigens on lamellar poly(lactide) adjuvants

| Antigen | % w/w adsorbed | Retained amount/time in vitro |
|---|---|---|
| Influenza virus | 19.0 | 65% at 8 weeks |
| Tetanus toxoid | 7.1 | 86% at 8 weeks |
| Ovalbumin | 7.3 | 97% at 4 weeks |

EXAMPLE 5

Immunogenicity of Vaccines Prepared by Adsorption of Influenza Virus on PLA Lamellar Substrates A/Shanghai/24/90 influenza virus was adsorbed to PLA lamellar substrate particles prepared by the methods of examples 1 and 3, and to prior art 75:25 PLG microspheres respectively. The adsorbed virus was allowed to stabilise for 14 weeks before commencing the immunogenicity study. The haemagglutinin (HA) content of the vaccines was calculated by estimating the amount of antigen remaining attached to the microparticles. The vaccine formulations were administered sub-cutaneously to groups of 20 Balb/C mice and test bleeds were obtained on day 28. All sera were tested for antibody to virus by haemagglutinin inhibition (HI).

The vaccine test formulations were as follows:

1. Aqueous inactivated virus. 15 $\mu$g HA/0.1 ml
2. Inactivated virus, adsorbed to PLG microspheres, 15 $\mu$g HA/0.1 ml
3. Inactivated virus, adsorbed to PLA lamellar adjuvant, 15 $\mu$g HA/0.1 ml The HI titre results are presented in Table 2. These results show that over a 10 fold improvement in antibody response to vaccines formulated with PLA lamellar particles according to the invention was found compared with soluble virus. In addition, the response to virus adsorbed on PLA lamellar particles was almost five times that obtained using prior art PLG microspheres as a substrate for adsorption of influenza virus.

TABLE 2

| | HI titres | | |
|---|---|---|---|
| Mouse Number | Group 1 (Aqueous) | Group 2 (755) | Group 3 (L) |
| 1 | 100 | 150 | 600 |
| 2 | 50 | 300 | 600 |
| 3 | <50 | 50 | 3200 |
| 4 | 50 | 200 | 2400 |
| 5 | 75 | 400 | 1600 |
| 6 | 100 | 150 | 2400 |
| 7 | 100 | 400 | 1200 |
| 8 | 150 | 300 | 2400 |
| 9 | 75 | 400 | 600 |

TABLE 2-continued

| | | | |
|---|---|---|---|
| 10 | 100 | 300 | 1200 |
| 11 | <50 | 100 | 1200 |
| 12 | 150 | 400 | 600 |
| 13 | 75 | 300 | 2400 |
| 14 | 50 | 75 | 400 |
| 15 | 100 | 400 | 2400 |
| 16 | 50 | 300 | 800 |
| 17 | 150 | 300 | 150 |
| 18 | 150 | 75 | 1200 |
| 19 | 100 | 400 | 600 |
| 20 | <50 | 200 | 800 |
| GMT | 71 | 221 | 1047 |

Statistical Analysis

Students t test
1. Comparison of group 1 with group 2
t = 5.55, significant at $P < 0.05$.
2. Comparison of group 1 with group 3
t = 12.0, significant at $P < 0.05$.
3. Comparison of group 2 with group 3
t = 7.60, significant at $P < 0.05$.

EXAMPLE 6

Thermal Analysis of Lamellar Substrates

Thermal transitions were recorded for PLA lamellar substrates and 75:25 PLG microspherical substrates using Differential Scanning Calorimetry. On heating at 20° C./min from 20° C. to 200° C. a single melting peak was observed at 130° C. for lamellae prepared using a low molecular weight polymer (Mw) (molecular weight 6600). The sample was then cooled to 20° C. at a rate of 80° C./min and reheated immediately at 40° C./minute. A re-crystallisation, exothermic peak was observed at 87° C. and a melting peak at 120° C.

PLA lamellar substrates prepared using a higher molecular weight polymer (MW 90,600) gave rise to a melting peak at 182° C. on heating. After cooling and reheating, a re-crystallisation peak was observed at 117° C. followed by a melting peak at 175° C.

The low melting temperature associated with the use of low molecular weight PLA material is indicative of small crystallite sizes and/or a higher degree of structural irregularity within the crystallites making up the lamellae.

The 75:25 PLG microspheres showed a glass transition at 60° C. on heating. After cooling and reheating the glass transition temperature was observed to have shifted to a slightly lower temperature of 57° C. The amorphous nature of the 75:25 PLG copolymer results in an absence of melting or re-crystallisation peaks on thermal analysis.

EXAMPLE 7

The Immune Response to Orally Administered Lamellae with Adsorbed Influenza Virus Two doses of influenza virus (A/Shanghai/24/90, 15 $\mu$g HA/0.1 ml dose) adsorbed to lamellar particles were administered orally to mice (20/group) at an interval of 56 days. Mice were treated orally with an oral antacid (Aludrax), 2 hours before the first vaccine dose and with an $H_2$-antagonist (Tagamet) parenterally 2 hours before the boost. The immune response was compared with that occurring in mice which received two doses of influenza virus adsorbed to 75:25 PLG microspheres and aqueous vaccine respectively. Microparticles without influenza virus were also administered as a control.

Test bleeds and nasal washes were taken on days 28 and 76.

All groups were challenged on day 80 by nasal/oral administration with 50 mouse infectious dose 50 (MID50) (A/Shanghai 24/90) virus.

Nasal washes were taken on days 1–7 after challenge and virus was titrated in MDCK cells.

Weak serum HI antibody responses were measured for all vaccinated groups at 28 and 76 days following vaccine administration (Table 3). The mice which received the adsorbed lamellae vaccine were significantly better protected against virus challenged than those which received aqueous vaccine or virus adsorbed on PLG microspheres.

TABLE 3

Immmunogenicity and protective effects for orally administered lamellar systems

Immunogenicity

| Vaccine | HA conc$^n$ ($\mu$g/0.1 ml) | No. of mice | 28 day GMT | 28 day No. of rises[1] | 76 day GMT | 76 day No. of rises |
|---|---|---|---|---|---|---|
| Aqueous | 15 | 20 | 69 | 7 | 47 | 9 |
| 755 | 14.6 | 15 | 68 | 4 | 47 | 4 |
| L | 14.4 | 19 | 65 | 7 | 50 | 6 |
| Particles | 0 | 20 | <25 | 0 | <25 | 0 |

[1]A post-immunisation HI titre ≧1:40

Protection

Virus shedding

| Vaccine | No. of mice | No. of mice | Mean duration (days) | Mean titre ($\log_{10}$) | Protection[1] |
|---|---|---|---|---|---|
| Aqueous | 20 | 19 | 4.9 | 2 | 5% |
| 755 | 15 | 14 | 3.3 | 1.5 | 7% |
| L | 19 | 13 | 2.8 | 1.2 | 32% |
| Particles | 19 | 19 | 5.1 | 2.1 | 0% |

[1]Based on virus shedding

EXAMPLE 8

Cumulative Release of Influenza Virus from PLA Lamellae

Influenza virus was adsorbed onto PLA lamellae (Mw 6600) using the method described in Example 3. The quantity of virus in the incubation medium was adjusted so as to achieve lamellae with virus loadings of 19% w/w and 13.1% w/w respectively. Influenza virus was also adsorbed onto lamellae prepared using a poly(L-lactide) polymer of Mw 90.600. An in vitro release study was conducted as described in Example 4. Cumulative release figures recorded for each sample are presented in Table 4 for comparison.

The amount of retained influenza virus in vitro may be controlled by adjusting the quantity of virus adsorbed to the lamellae any by varying the polymer molecular weight characteristics.

TABLE 4

Cumulative release of influenza virus from PLA lamellae
PLA Molecular weight (MW) 6600
Influenza virus adsorbed 19.0% (w/w)

| Time (Days) | 1 | 9 | 20 | 41 | 57 |
|---|---|---|---|---|---|
| % Release | 1.8 | 25.6 | 31.7 | 34.3 | 36.1 |

TABLE 4-continued

Cumulative release of influenza virus from PLA lamellae
PLA Mw 6600
Influenza virus adsorbed 13.1% (w/w)

| Time (Days) | 3 | 7 | 19 | 40 | 48 |
|---|---|---|---|---|---|
| % Release | 1.2 | 2.0 | 3.7 | 20.8 | 32.4 |

PLA Molecular weight (Mw) 90,600
Influenza virus adsorbed 20.6% (w/w)

| Time (Days) | 1 | 9 | 20 | 41 | 57 |
|---|---|---|---|---|---|
| % Release | 3.7 | 5.5 | 6.4 | 34.7 | 44.6 |

EXAMPLE 9

Cumulative Release of Tetanus Toxoid from PLA Lamellae

Tetanus toxoid was adsorbed onto PLA lamellae (Mw 90.600) using the method described in Example 3 to give an adsorbed load of 7.1% (w/w). An in vitro release study was conducted as described in Example 4. Cumulative release figures are presented in Table 5.

TABLE 5

Release of adsorbed tetanus toxoid from lamellar structures
PLA Molecular weight (Mw) 90,600
Tetanus toxoid adsorbed 7.1% (w/w)

| Time (Days) | 4 | 10 | 18 | 40 | 53 |
|---|---|---|---|---|---|
| % Release | 47 | 8.6 | 10.3 | 2.8 | 14.4 |

REFERENCES

Alpar H. O., Almeida A. J. Identification of some of the physico-chemical characteristics of microspheres which influence the induction of the immune response following mucosal delivery. Eur. J. Pharm. Biopharm. 40, 198–202 (1994).

Cohen S., Bernstein C., Hewes C., Chow M., Langer R. The pharmacokinetics of and humoral responses to antigen delivered by microencapsulated lipsomes. Proc. Natl. Acad. Sci. U.S.A. 88, 10440–10444 (1991).

Eldridge J. H., Staas K., Meulbroek J. A., McGhee R., Tice T. R., Gilley R. M. Biodegradable microspheres as a vaccine delivery system. Mol. Immunol. (1991), 28, 287–294.

Espartza I., Kissel T. Parameters affecting the immunogenicity of microencapsulated tetanus toxoid. Vaccine (1992) 10, 714–720.

Gray D., Skarvall H. B-cell memory is short lived in the absence of antigen. Nature, (1988) 336, 70.

Khan M. Z. I. Optebeeck J. P., Tucker I. G. Immunopotentiation and delivery systems for antigens for single-step immunisation. Recent trends and progress. Pharm. Res., 11, (1994) 2–11.

Kreuter J., Liehl E., Berg U., Soliva M., Speiser P. P. Influence of hydrophobicity on the adjuvant effect of particulate polymeric adjuvants. Vaccine, (1988) 6, 253–256.

O'Hagan D. T., Dahman D., McGee P., Jeffery H., Davies M. C., Williams P., Davis S. S., Challacombe S. J. Biodegradable microparticles as controlled release antigen delivery systems. Immunology, 73, 239–242 (1991).

O'Hagan D. T., Jeffery H., Davis S. S. Long term antibody responses in mice following subcutaneous immunisation with ovalbumin entrapped in biodegradable microparticles. Vaccine, 11, (1993) 965–969.

Park T. G., Lu W. L., Crotts G. Importance of in vitro experimental conditions on protein release kinetics, stability and polymer degradation in protein encapsulated poly(DL lactic acid co-glycolic acid) microspheres. J. Controlled Rel., 33 (1995) 211–222.

Raghuvanshi R. S., Singh M., Talwas G. P. Biodegradable delivery system for single step immunisation with tetanus toxoid, Int. J. Pharm., 93 (1993) R1–R5.

Stieneker F., Kersten G., van Bloois L., Crommelin D. J. A., Hem S. L., Lower J., Kreuter J. Comparison of 24 different adjuvants for inactivated HIV-2 split whole virus as antigen in mice. Induction of titres of binding antibodies and toxicity of the formulations. Vaccine, (1995) 13, 45–53.

We claim:

1. A composition for delivery of an active agent comprising
    a plurality of lamellar particles comprising a biodegradable polymer which is at least partially crystalline, and
    an active agent adsorbed to at least a majority of the particles.

2. The composition of claim 1 wherein the biodegradable polymer is at least 5 percent by weight crystalline.

3. The composition of claim 1 wherein the biodegradable polymer comprises a mixture of two or more biodegradable polymers which are at least partially crystalline.

4. The composition of claim 1 wherein the biodegradable polymer is poly(L-lactide).

5. The composition of claim 1 wherein the biodegradable polymer is a copolymer of poly(L-lactide).

6. The composition of claim 1 wherein the active agent is selected from the group consisting of DNA, antigens, allergens, and vaccines.

7. The composition of claim 6 wherein the antigen is selected from the group consisting of Tetanus toxoid and influenza virus.

8. The composition of claim 1 wherein the active agent is selected from the group consisting of peptides, polypeptides and proteins.

9. The composition of claim 8 wherein the active agent is selected from the group consisting of DNA, insulin, luteinizing hormone releasing factor, growth factors, hormones, interferons, interleukins, and somatostatins.

10. The composition of claim 8 wherein the lamellar particles and adsorbed active agent are coated with a polymer.

11. The composition of claim 1 wherein at least a portion of the lamellar particles are coalesced.

12. The composition of claim 1 wherein the lamellar particles have a thickness in the range of between about 50 nm and about 80 μm.

13. A method of making a composition for delivery of an active agent comprising the steps of:
    a) dissolving a polymer in a solvent to form a polymer solution;
    b) stirring the polymer solution vigorously and adding a non-solvent for the polymer to form a mixture;
    c) evaporating the solvent from the mixture thereby forming lamellar particles; and
    d) admixing an active agent with the lamellar particles.

14. The method of claim 13 wherein the solvent is selected from the group consisting of acetone, ethyl acetate, xylene and dioxane.

15. The method of claim 13 wherein the non-solvent is selected from the group consisting of water, methanol, and ethanol.

16. The composition of claim 1 wherein the biodegradable polymer is at least 30 percent by weight crystalline.

17. The composition of claim 1 further comprising a surface modifying agent.

18. A method of making a composition for delivery of an active agent comprising the steps of:
    a) dissolving a polymer in a solvent to form a polymer solution;
    b) cooling the polymer solution to crystallize the polymer in the form of lamellar particles; and
    c) admixing an active agent with the lamellar particles.

* * * * *